(12) United States Patent
Agazie et al.

(10) Patent No.: US 7,547,760 B2
(45) Date of Patent: Jun. 16, 2009

(54) PEPTIDES AND CHEMICAL COMPOUND FOR INHIBITION OF SHP2 FUNCTION

(75) Inventors: Yehenew Mekonnen Agazie, Morgantown, WV (US); Peter M. Mannett, Morgantown, WV (US)

(73) Assignee: West Virginia University, Morgantown, WV (US)

( * ) Notice: Subject to any disclaimer, the term of this patent is extended or adjusted under 35 U.S.C. 154(b) by 0 days.

(21) Appl. No.: 11/480,814

(22) Filed: Jul. 3, 2006

(65) Prior Publication Data

US 2008/0004215 A1    Jan. 3, 2008

(51) Int. Cl.
*A61K 38/04* (2006.01)
*A61K 38/00* (2006.01)
*C07K 1/00* (2006.01)
*C07K 14/00* (2006.01)
*C07K 2/00* (2006.01)

(52) U.S. Cl. .................. 530/330; 530/300; 530/331; 530/345

(58) Field of Classification Search ................ None
See application file for complete search history.

(56) References Cited

U.S. PATENT DOCUMENTS

| | | | |
|---|---|---|---|
| 6,200,807 B1 | 3/2001 | Bennett et al. | |
| 6,270,981 B1 | 8/2001 | Carpenter et al. | |
| 6,756,478 B2 | 6/2004 | Valladeau et al. | |
| 6,849,420 B2 | 2/2005 | Vanhasebroeck et al. | |
| 7,026,283 B2 | 4/2006 | Fleming et al. | |
| 2004/0265910 A1* | 12/2004 | Haaland et al. | 435/7.1 |

FOREIGN PATENT DOCUMENTS

WO    WO2004020466 A1 *    3/2004

OTHER PUBLICATIONS

Burgess, Shaheen, Ravera, Jaye, Donohue, and Winkles. Possible dissociation of the heparin-binding and mitogenic activities of heparin-binding (acidic fibroblast) growth factor-1 from its receptor-binding activites by site-directed mutagenesis of a single lysine residue. Journal of Cell Biology, 1990. vol. 111, pp. 2129-2138.*
Lazar, E., Watanabe, S., Dalton, S., and Sporn, M.B. Transforming growth factor a: mutation of aspartic acid 47 and leucine 48 results in different biological activities. Molecular and Cellular Biology, 1988. vol. 8 No. 3, pp. 1247-1252.*
Schwartz, G.P., Burke, G.T., and Katsoyannis, P.G. A superactive insulin: [B10-aspartic acid]insulin (human). Proceedings of the National Acacdemy of Sciences, 1987. vol. 84, pp. 6408-6411.*
Lin, M.C., Wright, D.E., Hruby, V.J., and Rodbell, M. Structure-function relationships in glucagon: properties of highly purified Des-His1-, Monoiodo-, and [Des-Asn28, Thr29](homoserine lactone27)-glucagon. Biochemistry, 1975. vol. 14, No. 8, pp. 1559-1563.*
Qin, C., Wavreille, A., and Pei, D. Alternative mode of binding to phosphotyrosyl peptides by Src Homology-2 domains. Biochemistry, 2005. vol. 44, pp. 12196-12202.*
Imhof, D., Wavreille, A., May, A., Zacharias, M., Tridandapani, S., and Pei, D. Sequence specficity of SHP1 and SHP2 Src homology 2 domains. Journal of Biological Chemistry, 2006. vol. 281 No. 29, pp. 20271-20282.*
Lesuisse, Lange, Deprez, Benard, Schoot, Delettre, Marquette, Broto, Jean-Baptiste, Bichet, Sarubbi, and Mandine. SAR and X-ray. A new approach combining fragment-based screening and rational drug design: application to the discovery of nanomolar inhibitors of Src SH2. Journal of Medicinal Chemistry, 2002. vol. 45, pp. 2379-2387.*

* cited by examiner

*Primary Examiner*—David J. Blanchard
*Assistant Examiner*—Anne M. Gussow
(74) *Attorney, Agent, or Firm*—William Aylor

(57) ABSTRACT

The present invention relates to the inhibition of the function of SHP2 by both anti-SHP2 peptides and the chemical compound 4-(2-sulfaminoethyl)benzoic acid, SEBA, and SEBA derivatives binding to the phosphotyrosyl phosphatase domain of SHP2 thereby inhibiting the function of SHP2 both in vitro and in vivo. In addition, the inhibition of SHP2 may be useful as a treatment for human disease, and it has been shown that interfering with SHP2 function using the anti-SHP2 peptides and SEBA compounds reverses cell transformation and induces remission of preformed tumors in vivo demonstrating a possible treatment for cancer.

7 Claims, 13 Drawing Sheets

No Si-RNA　　Si-RNA - Tet　　Si-RNA + Tet　　MCF10A
BT474　　　　BT474

Acetate   Phosphate   Sulfate   Amino-sulfate

Figure 10

R: Asp-Gly-Asp-Gly, Asp-Ala-Asp-Ala, Asp-Val-Asp-Val, Asp-Ala-Asp-Val, Asp-Ala-Asp-Gly, Asp-Gly-Asp-Val, Asp-Gly-Asp-Ala, Asp-Val-Asp-Gly, Asp-Val-Asp-Ala, Asp-Ala, Asp-Gly, Asp-Val or their modified versions.

SEQUENCE LISTING

```
<160> NUMBER OF SEQ ID NOS: 5

<210> SEQ ID NO 1
<211> LENGTH: 5
<212> TYPE: PRT
<213> ORGANISM: Homo sapiens

<400> SEQUENCE: 1

Asp Ala Asp Val Tyr
1               5

<210> SEQ ID NO 2
<211> LENGTH: 5
<212> TYPE: PRT
<213> ORGANISM: Homo sapiens

<400> SEQUENCE: 2

Asp Ala Asp Gly Tyr
1               5

<210> SEQ ID NO 3
<211> LENGTH: 5
<212> TYPE: PRT
<213> ORGANISM: Homo sapiens

<400> SEQUENCE: 3

Glu Ala Asp Val Tyr
1               5

<210> SEQ ID NO 4
<211> LENGTH: 3
<212> TYPE: PRT
<213> ORGANISM: Homo sapiens

<400> SEQUENCE: 4

Asp Val Tyr
1

<210> SEQ ID NO 5
<211> LENGTH: 3
<212> TYPE: PRT
<213> ORGANISM: Homo sapiens
```

```
<400> SEQUENCE: 5

Asp Gly Tyr
1
```

PEPTIDES AND CHEMICAL COMPOUND FOR INHIBITION OF SHP2 FUNCTION

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

The Sequence Listing attached at the end of the application is the written sequence listing as is identical to the computer readable form.

BACKGROUND OF THE INVENTION

1. Field of Invention

This invention relates to the inhibition of the function of SHP2 by anti-SHP2 peptides, the chemical compounds 4-(2-sulfaminoethyl)benzoic acid ("SEBA"), and SEBA derivatives binding to the phosphotyrosyl phosphatase domain of SHP2.

2. Description of the Prior Art

Protein Tyr phosphorylation and dephosphorylation reactions play major role in the transduction of growth factor signals from the surface to the interior of the cell. Phosphorylation involves addition of a phosphate moiety to the hydroxyl group of the Tyr residue in proteins or peptides, while dephosphorylation refers to the removal of such phosphate from the phosphotyrosine. Phosphorylation reactions are catalyzed by Tyr kinases, while dephosphorylation reactions are catalyzed by phosphotyrosyl phosphatases ("PTPs"). Depending on their location in the cell, Tyr kinases are generally classified as cytoplasmic Tyr kinases ("CTKs") or receptor Tyr kinases ("RTKs"). Most commonly cited CTKs include Src, focal adhesion kinase ("FAK") and janus kinases ("JAKs") (17, 19, 47, 72, 73), while the most commonly studied RTKs are the epidermal growth factor receptor ("EGFR") family, the platelet growth factor receptor ("PDGFR") family, the fibroblast growth factor receptor ("FGFR") family and the insulin receptor (30, 45, 82, 96). Similarly, PTPs are classified as cytoplasmic or receptor type depending on their location in the cell (7, 8, 66, 93). This invention focuses on SHP2, the cytoplasmic PTP that has been shown to positively modulate RTK signaling, particularly, signaling by the epidermal growth factor receptor ("EGFR") family.

SHP2 possesses two tandemly-arranged Src homology 2 ("SH2") domains in the N-terminal region and a PTP domain in the C terminal region (32, 33). Both of these domains are essential for its biological activity (14, 32, 33, 78, 79, 86). It also possesses two tyrosine phosphorylation sites and a proline-rich motif (—PXXP—) in the extreme C-terminal region (10, 29, 69). The SHP2 protein assumes a "closed conformation" when inactive and an "open conformation" when active. In the closed conformation, the N-SH2 domain interacts with the PTP domain thus physically impeding the PTP domain from binding to target substrates. Upon engagement of the N-SH2 domain with phosphotyrosyl residues, the protein assumes an open conformation, relieving the PTP domain and rendering the enzyme active (41). In the N-SH2 domain, Asp61 and Glu76 are the mediators of this interaction. As a result, mutation of these residues creates a constitutively active SHP2 (70). Recent findings show that constitutively active SHP2 mutatants naturally occur in Noonan Syndrome-associated leukemia (87-89).

In the catalytic process of most PTPs, including SHP2, Asp in the WPD loop and the conserved residues in the signature motif play critical roles in the dephosphorylation reaction (34). In SHP2, Asp425 acts as a proton donor for the leaving phenolate group of the substrate and as an acceptor during the hydrolysis of the cysteinyl phosphate intermediate. The Cys residue conducts a nucleophilic attack on the phosphate moiety, while the Arg residue (positively charged) serves as a coordinator of the negatively charged phosphate group on the substrate. Basically, the Arg residue mediates substrate binding to the active site of the enzyme, whereas the Cys and Asp residues catalyze the dephosphorylation reaction. In addition, Thr466 is essential for SHP2 catalysis (61), but its specific role has not been established. Mutation of this residue to Ala provides a new substrate-trapping mutant of SHP2 (61). SHP2 is a unique PTP that positively modulates RTK signaling in vertebrates (32, 33, 35, 38). Interaction of SHP2 with Tyr-phosphorylated RTKs and adaptor proteins such as Gab1 and 2 and FRS1 and 2 through its SH2 domains is important for its function (28, 38, 51, 55, 80, 92). This interaction recruits SHP2 to its substrate microdomain. Deletion of the N-SH2 domain or mutation of critical residues in the active site of the enzyme such as Cys459 to Ser or Arg465 to Glu inactivates SHP2, suggesting that both domains are important for its function. These mutants have served as dominant-negative counterparts ("DN-SHP2") in SHP2 studies as their expression inhibits the activation of the Ras-ERK (ERK for extracellular signal regulated kinase 1 and 2) and the PI3K-Akt (PI3K for phosphatidylinositol 3-kinase) signaling pathways downstream of RTKs (5, 6, 53, 54, 92).

SHP2 enhances the signaling potential of the EGFR family of RTKs. The EGFR family comprises four members ("EGFR1-4") and represents one of the most extensively studied RTKs in the mammalian system (30, 48, 57, 58, 82, 95). The human homologues are called HER1, HER2, HER3 and HER4. Because HER1 is commonly known as EGFR, this abbreviation will be used hereinafter. All family members are composed of an extracellular ligand-binding region, a single-pass transmembrane region and a cytoplasmic region containing a tyrosine kinase domain (except HER3 that has dysfunctional kinase domain) and tyrosine autophosphorylation sites. A family of a dozen growth factors, including epidermal growth factor ("EGF"), transforming growth factor-α ("TGFα") and neuregulins, activate these receptors by binding to the extracellular region (except HER2 that does not require ligand binding for activation). The binding of a cognate ligand induces homo- or hetero-dimerization of EGFR molecules leading to the activation of their tyrosine kinase domain and autophosphorylation of specific tyrosine residues in the C-terminal region or Tyr phosphorylation of downstream substrates (24, 26, 28, 43, 51, 59, 71). Phosphorylated tyrosine residues serve as binding sites for SH2 domain-containing signaling molecules such as the Grb2-SOS complex, the phosphatidylinositol 3-kinase ("PI3K"), SHP2 and others (74), which leads to formation of multimeric signaling complexes. At least two known functions are effected by these interactions: recruitment of enzymes to substrate micro domains (e.g. Grb2-SOS) and induction of enzyme activity (egs. PI3K, SHP2) (2, 12, 33, 38, 55, 59, 80, 83). The immediate response to stimulation with EGF or the related ligands is the activation of the Ras-ERK (ERK for extracellular regulated kinase 1 and 2) and the PI3K-Akt (Akt is sometimes referred to as protein kinase B) signaling pathways, which induce mitogenesis and cell survival, respectively. Structural and biochemical analyses have shown that HER2 does not require ligand binding for activation of its tyrosine kinase domain (36). Thus, HER2 can potentially homodimerize in the absence of ligand (especially under conditions of overexpression) or heterodimerize with ligand-stimulated family members. Generally, HER2 is regarded as the preferred partner of heterodimerization with the other family members most probably due to the unconstrained conformation of the dimerization arm of the extracellular region (36). In case of HER3, heterodimerization with other family member is the only mechanism for its activation because it lacks a functional Tyr kinase domain (42).

Regulation of cell shape and morphology by SHP2 has been correlated with its effect on actin cytoskeletal reorganization. Cells expressing dominant-negative SHP2 manifest an increased level of actin stress fiber formation and assume a flattened morphology, whereas cells expressing wild-type SHP2 show a low level of actin stress fiber formation and a more polarized morphology (46, 50, 84). These effects of SHP2 have been ascribed to its negative regulatory role of the Rho GTPase (25, 52, 84).

SHP2 suppresses cell adhesion and enhances motility (46, 50, 56, 102). However, the molecular basis underlying these effects is not clear. Cell migration requires a coordinated cycling between adhesion and detachment. In a tissue or in confluent monolayer of cultured cells, movement of a single cell in a defined direction involves modulation of its interaction with neighboring cells and the extracellular matrix ("ECM"). Adhesion of cells to the ECM is mediated by cell surface receptors called integrins. Integrin-ECM interaction recruits cytoplasmic tyrosine kinases ("CTK") such as FAK, related focal tyrosine kinase ("RFTK") or Pyk2 and Src (72, 81) to the plasma membrane. Autophosphorylation of FAK initiates the cascade of tyrosine phosphorylation reactions by recruiting Src to focal adhesions (72, 81). The adaptor proteins p130$^{Cas}$ and paxillin are the other major proteins known to participate in focal adhesion formations. The SH3 and Src-binding domains of p130$^{Cas}$ mediate interaction with FAK and Src, which in turn mediate Tyr phosphorylation (65, 76). Paxillin possesses lucine-rich motifs that promote its interaction with FAK and the other focal adhesion protein vinculin (21, 27). Paxillin also possesses Tyr phosphorylation sites that mediate SH2 domain interactions (99). The net effect is the aggregation of integrins, the formation of multiprotein complexes and the maturation of focal complexes to focal adhesions (56, 100). SHP2 has been repeatedly implicated in down regulating focal adhesions, but the molecular mechanism is not clear.

SHP2 mediates cell transformation induced by v-Src (39) and the constitutively active form of fibroblast growth factor receptor 3 (K650E-FGFR3) (6). In K650E-FGFR3-induced transformation, SHP2-mediated activation of the Ras-ERK and PI3K-Akt pathways was essential. Recently, it was demonstrated that SHP2 promotes K650E-FGFR3-induced transformation not only by promoting the activation of the Ras-ERK and PI3K-Akt pathways, but also by modulating the interaction of the actin cytoskeleton with adherens junction (23). The recent discovery of gain-of-function SHP2 mutations in Noonan syndrome and associated leukemia (15, 62, 89) and the subsequent demonstration of the development of lymphoid hyperplasia in transgenic mice expressing gain-of-function SHP2 mutants (9, 62) further support the importance of SHP2 in cancer.

The driving force behind this invention is that SHP2 is an essential transducer of cell transformation induced by Tyr kinase oncogenes, which in turn suggests that it promotes tumor growth. Recent reports have uncovered molecular mechanisms by which the phosphatase activity of SHP2 promotes signaling by Tyr kinases, particulary by the EGFR. The development of a substrate-trapping mutants of SHP2 was a breakthrough for understanding its molecular mechanism (4). Substrate trapping refers to the production of mutant phosphatases that retain substrate-binding ability or acquire enhanced substrate-binding ability, but are devoid of enzyme activity (34). Thus, by introducing mutations in the active site of SHP2, an efficient substrate trapping mutant termed DM-SHP2 (DM for double mutant) was developed (4). Using the DM-SHP2 as a reagent, the first biological substrate of SHP2, the EGFR, was identified and characterized. Subsequently, a molecular mechanism for SHP2 in promoting EGFR signaling was described. It was demonstrated that SHP2 promotes Ras activation by interfering with the process of Ras inactivation catalyzed by the Ras GTPase activating protein (RasGAP). Inhibition is achieved through the dephosphorylation of Tyr992 of the EGFR, which serves as RasGAP binding site (5).

Substrate-trapping and mass spectroscopic analysis showed that α-catenin also is a biological substrate of SHP2 (23). Tyr phosphorylation of α-catenin enhances its translocation to the plasma membrane and its interaction with β-catenin, leading to enhanced actin polymerization and stabilization of adherens junction-mediated intercellular adhesion, a phenomenon commensurate with loss of the transformation phenotype. Dephosphorylation of α-catenin by SHP2 suppresses intercellular adhesion and increases the cytosolic pool of β-catenin and its subsequent translocation to the nucleus (23) where it acts as a transcription factor for mitogenic genes such as cyclin D1 and c-myc (1, 13). In addition, inhibition of α-catenin enhances activation of the Ras-ERK and the PI3K-Akt pathways (23, 97), induces hyperproliferation of skin epithelium (97) and promotes cell transformation (22, 63). Therefore, SHP2 mediates β-catenin activation downstream of RTKs bypassing the need for Wnt ligand stimulation (23). The previously held notion was that β-catenin is activated downstream of the frizzled (FZ) and low-density lipoprotein related protein ("LRP$^{5/6}$") coreceptors following Wnt ligand stimulation (18, 49, 60).

In EGFR and HER2, SHP2 dephosphorylates negative-regulatory phosphorylation sites that serve as RasGAP binding sites. By doing so, SHP2 promotes the Ras-ERK and the PI3K-Akt signaling pathways (5). In α-catenin, SHP2 dephosphorylates a phosphotyrosyl that mediates interaction with β-catenin (23). This leads to suppression of adherens junction-mediated cell-cell interaction, an increase in cytosolic β-catenin pool and subsequent translocation of β-catenin to the nucleus where it acts as a transcription factor for mitogenic genes. Thus, through SHP2, EGFR and HER2 can activate, not only the Ras-ERK and the PI3K-Akt pathways, but also β-catenin signaling. Therefore, mediation of cell transformation by SHP2 is a complex process that involves modulation of the Ras-ERK and PI3K-Akt signaling pathways, intercellular adhesion, focal adhesion and actin cytoskeletal reorganization. These findings suggest that SHP2 could be a potential target for cancer treatment.

Examples that highlight the importance of SHP2 in growth factor signaling, cell transformation and cancer development are provided below. These results were based on inhibition of SHP2 either by dominant-negative SHP2 (DN-SHP2) expression or small interfering RNA (Si-RNA)-mediated ablation of the SHP2 protein. As known in the art, DN-SHP2 expression refers to ectopic expression of a dysfunctional mutant protein that competes with the endogenous counterpart and inhibits function. The controls for these experiments were vector alone and the wild type form of SHP2 (WT-SHP2). The indicated breast cancer cell lines were infected with retrovirus expressing vector alone, WT-SHP2 or DN-SHP2, and stable lines from each group were seeded in soft agar, a commonly used assay for testing anchorage-independent growth (3, 23). The MCF10A, the immortalized normal breast cell line, was used as a negative control for anchorage-independent growth. Expression of DN-SHP2 inhibited colony formation by all of the breast cancer cells used in this experiment, while expression of vector alone or WT-SHP2 did not cause any change (FIG. 1), As expected, the negative control MCF10A cells could not form colonies in soft agar during anchorage-independent growth studies. In addition, expression of DN-SHP2 modestly suppressed cell growth in all of the cells used in this study (FIG. 2). Together, these results show that SHP2 is important for cell proliferation and anchorage-independent growth of breast cancer cells.

The importance of SHP2 in cell transformation and growth factor signaling was further investigated by Si-RNA-mediated ablation of the SHP2 protein in the BT474 breast cancer cells that overexpress the HER2 oncogene. As known in the art, expression of Si-RNA in cells inhibits the translation of the corresponding messenger RNA (mRNA) by hybridizing to a specific complementary region within the mRNA. For the current work, stable cell lines harboring the SHP2 Si-RNA were produced by infection of the BT474 cells with retroviruses expressing the SHP2 Si-RNA under the control of a tetracycline-inducible system (BD Biosceinces). These cells express the SHP2 Si-RNA only when they were treated with tetracycline. Parent BT474 cells were used as controls (control) in these experiments. In addition, cells harboring the SHP2 Si-RNA (non-Si-RNA), but not treated with tetracycline were used as controls for the effect of retroviral infection and gene integration. Therefore, the experimental groups used in these studies included controls, non-Si-RNA and Si-RNA cells. Si-RNA-mediated ablation of the SHP2 protein induced reversion of the BT474 cells to a normal phenotype that compares with the cobblestone-like appearance of the MCF10A, the immortalized normal breast epithelial cell line (FIG. 3). It also inhibited anchorage independent growth in soft agar (FIG. 4) and led to re-differentiation of the BT474 cells back to normal as evidenced by acini formation in laminin-rich basement membrane (LRBM) cultures (FIG. 5). It should be noted that Si-RNA cells die in soft agar, but re-differential to normal under adherent two dimensional and LRBM cultures. These results demonstrate that SHP2 is important for the maintenance of the transformation phenotype of breast cancer cells. In addition, they show that interference with SHP2 function leads to re-differentiation of breast cancer cells to a normal phenotype.

In addition to morphological and growth behavior changes, Si-RNA-mediated ablation of the SHP2 protein inhibited EGF-induced signaling. The indicated cells were grown to subconfluency, serum starved for about 12 hours and then stimulated with 10 ng/ml EGF for varying time points. Lysates prepared from these cells were separated by denaturing polyacrylamide gel electrophoresis, transferred onto a nitrocellulose membrane and analyzed by western blotting with antibodies that recognize the activated forms of ERK1/2 and Akt. Si-RNA-mediated ablation of the SHP2 protein inhibited EGF-induced activation of these proteins (FIG. 6), suggesting that SHP2 is required for mitogenic and cell survival signals in breast cancer cells. Therefore, SHP2 has the potential to serve as a new drug target for the treatment of breast cancer.

BRIEF DESCRIPTION OF THE SEVERAL VIEWS OF THE DRAWING

FIG. 10 are the oligopeptides for modification at the R position of SEBA derivatives.

BRIEF SUMMARY OF THE INVENTION

The present invention pertains to the inhibition of SHP2 in vivo and in vitro. The mechanism of inhibition is the binding of specific inhibitors to the active of SHP2.

The present invention further details peptides that can inhibit the function of SHP2. The anti-SHP2 peptides are oligopeptides that are 3-5 amino acids long, in their native form or their conservative variants. These peptides have been given a common name termed WGMDY Another aspect of the present invention is the ability to modify the anti-SHP2 peptides to create conservative variants. In this application the modification to create a conservative variant means: a) replacement of one amino acid by another to create a conservative variant; b) addition of a phosphate, a sulfate, amino-sulfate or an acetyl group to the single Tyr residue, c) introducing changes to side chains of amino acids, and d) making changes to the peptide backbone of the peptides.

Figure 8:
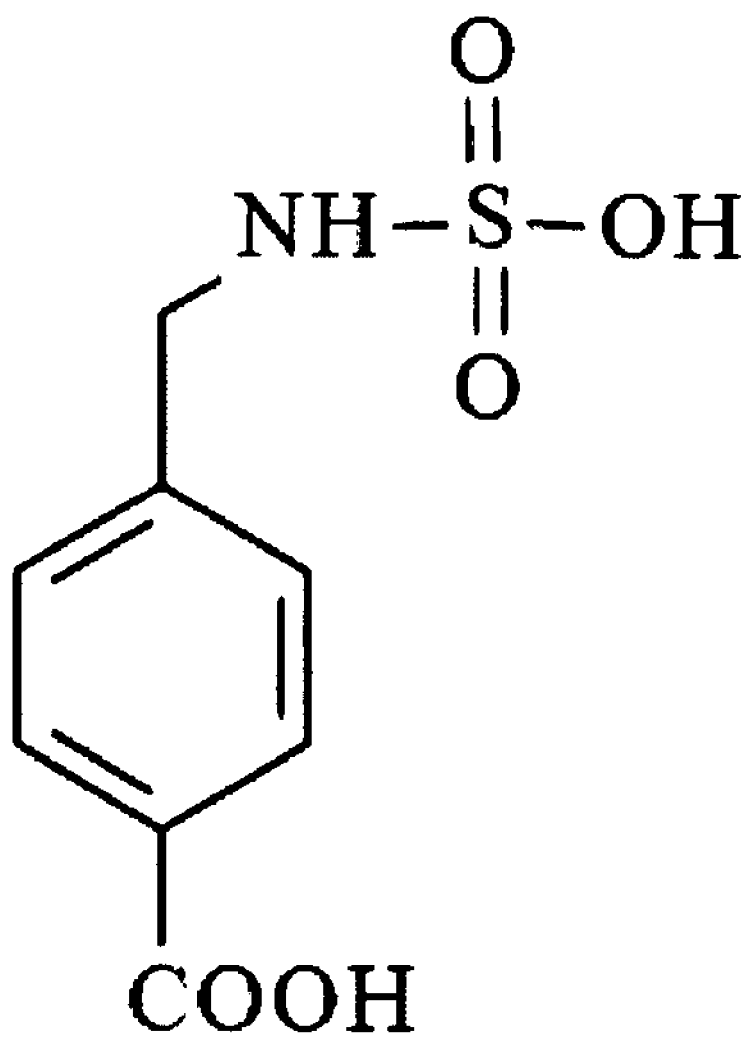
FIG. 8 is 4-(2-sulfaminoethyl) benzoic acid (SEBA).

Another object of the present invention is the chemical compound 4-(2-sulfaminoethyl)benzoic acid, SEBA (FIG. 8), and the use of this compound with anti-SHP2 function.

Another aspect of the present invention is the use of SEBA derivatives in the inhibition of the SHP2 function. The SEBA derivatives have the chemical formula

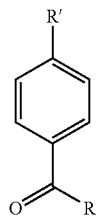

wherein R is selected from the functional group consisting of the amino acids sequence D-V; D-G; D-A; D-G-D-G; D-A-D-A; D-V-D-V; D-A-D-V; D-A-D-G; D-G-D-V; D-G-D-A; D-V-D-G; and D-V-D-A (also see FIG. 10) and R' is selected from the functional groups acetate; phosphate, sulfate, and aminosulfate (also see FIG. 7).

A further aspect of the invention is the inhibition of SHP2 in the treatment of human disease, namely cancer.

DETAILED DESCRIPTION OF THE INVENTION

The present invention involves 1) anti-SHP2 peptides and their conservative variants and 2) a peptidomimetic anti-SHP2 compound SEBA and its derivatives for use in inhibiting SHP2 function both in vitro and in vivo. It also teaches that SHP2 is a potential therapeutic target for the treatment of cancer and that interfering with SHP2 function using the anti-SHP2 peptides and SEBA compounds reverses cell transformation and induces remission of preformed tumors in vivo. As used herein, the term anti-SHP2 peptides refers to oligopeptides that are 3-5 amino acids long, in their native form or their conservative variants. These peptides have been given a common name termed WGMDY. Conservative variants of WGMDY peptides means: a) replacement of one amino acid by another to create a conservative variant; b) addition of a phosphate, a sulfate, amino-sulfate or an acetyl group to the single Tyr residue, c) introducing changes to side chains of amino acids, and d) making changes to the peptide backbone of the peptides. Detailed sequences of WGMDY peptides (FIG. 7) and functional groups for modification at the Y (Tyr) residue (FIG. 8) are provided.

| WGMDY peptides |
|---|
| SEQ ID: 1 |
| LENGTH: 5 |
| SEQUENCE: Asp-Ala-Asp-Val-Tyr |
| SEQ ID: 2 |
| LENGTH: 5 |
| SEQUENCE: Asp-Ala-Asp-Gly-Tyr |
| SEQ ID: 3 |
| LENGTH: 5 |
| SEQUENCE: Glu-Ala-Asp-Val-Tyr |
| SEQ ID: 4 |
| LENGTH: 3 |
| SEQUENCE: Asp-Val-Tyr |

| WGMDY peptides |
|---|
| SEQ ID: 5 |
| LENGTH: 3 |
| SEQUENCE: Asp-Gly-Tyr |

Conservative amino acid substitutions within the context of the application are shown in the table below and can be used to create conservative variants which have changes in the amino acid sequence, but are similar in function due to the conservative nature of the change. A conservative change is best described as the substitution of an acidic amino acid for an acidic amino acid or a hydrophobic amino acid for a hydrophobic amino acid. The exchange of an amino acid for another amino acid of similar chemical properties creates a conservative variant.

| Amino Acid | Conservative variants |
|---|---|
| Aspartic Acid, Asp, D | Glutamic Acid, Glu, E |
| Glycine, Gly, G | Alanine, Ala or A |
| Alanine, Ala, A | Glycine, Gly, G |
|  | Valine, Val, V |
|  | Leucine, Leu, L |
|  | Isoleucine, Ile, I |
| Valine, Val, V | Glycine, Gly, G |
|  | Alanine, Ala, A |
|  | Leucine, Leu, L |
|  | Isoleucine, Ile, I |
| Tyrosine, Tyr, Y | Phenylalanine, Phe, F |

Figure 9:
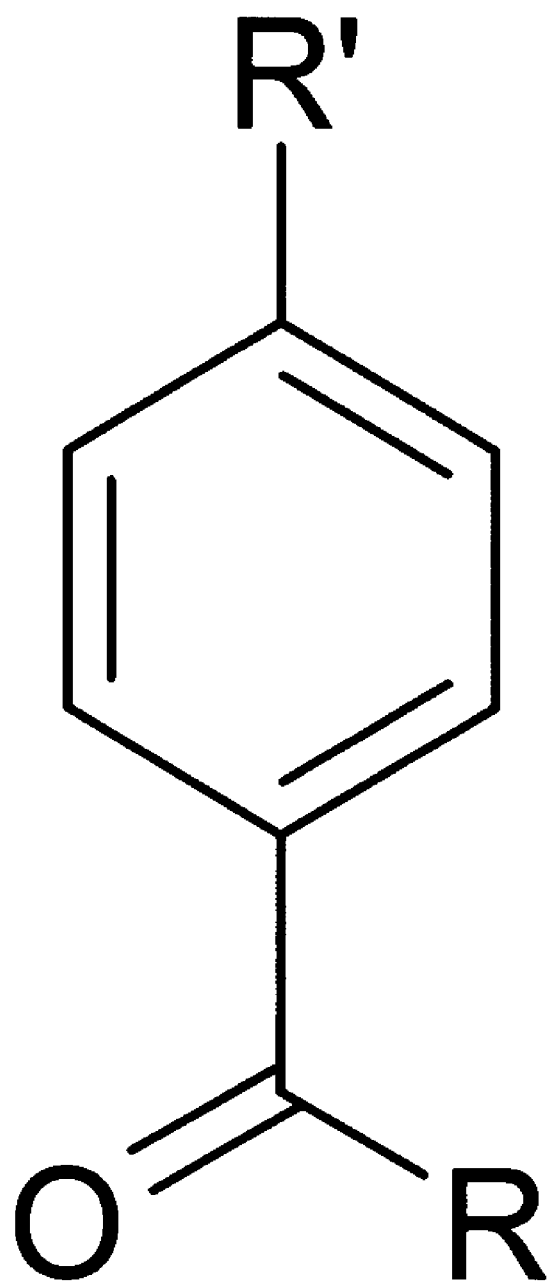
FIG. 9 are the SEBA derivatives

As also used herein, the term SEBA refers to 4-(2-sulfaminoethyl)benzoic acid (FIG. 8), while the term SEBA derivatives refers to modified version of SEBA derivative shown in FIG. 9. Modifications to produce SEBA derivatives include covalent linkage of functional groups of FIG. 7 to the R' and amino acid oligomers or their modified counterparts of FIG. 11 to the R. Modifications to amino acid oligomers linked to the R position refer to changes to the peptide bonds so as to confer resistance to peptidases or proteases, addition of hydrophobic groups or penetrating peptide sequences to enhance cellular uptake and changes to side chains of constituent amino acids to increase binding affinity to the target. In this context, the target is the active site of the SHP2 phosphatase domain.

In the context of the present invention, inhibition of SHP2 with WGMDY peptides and SEBA compounds refers to interfering with the normal function of SHP2. Inhibition is achieved by physical interaction of the WGMDY peptides and SEBA compounds with the active site of the phosphotyrosyl phosphatase domain of SHP2. This interaction blocks the binding of biological substrates to the same site. The overall effect is an increase in the Tyr phosphorylation level of biological substrates, leading to abrogation of the signal transducer role of SHP2. As described in the background and supporting evidences, the major signaling networks that are affected by SHP2 inhibition are the Ras-ERK, the PI3K-Akt and β-catenin signaling pathways. Consequently, promotion of cell proliferation, survival, transformation, migration and tumor growth by SHP2 is inhibited. The outstanding findings presented in FIGS. 1-6 clearly show that inhibition of SHP2 has the potential for the treatment of cancer. In addition, recent reports by the inventor (5, 23, 61) lend further support to this invention.

Figure 1:
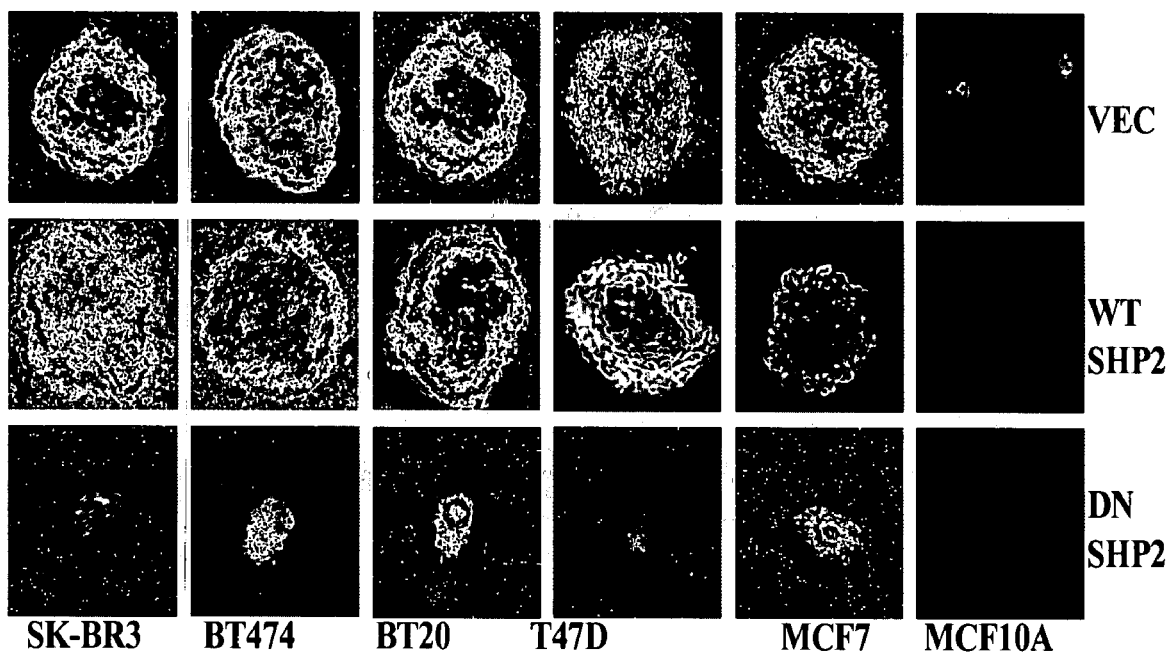
FIG. 1 is a colony formation in soft agar by several breast cancer cells expressing vector alone, WT-SHP2 and DN SHP2.
Figure 2:
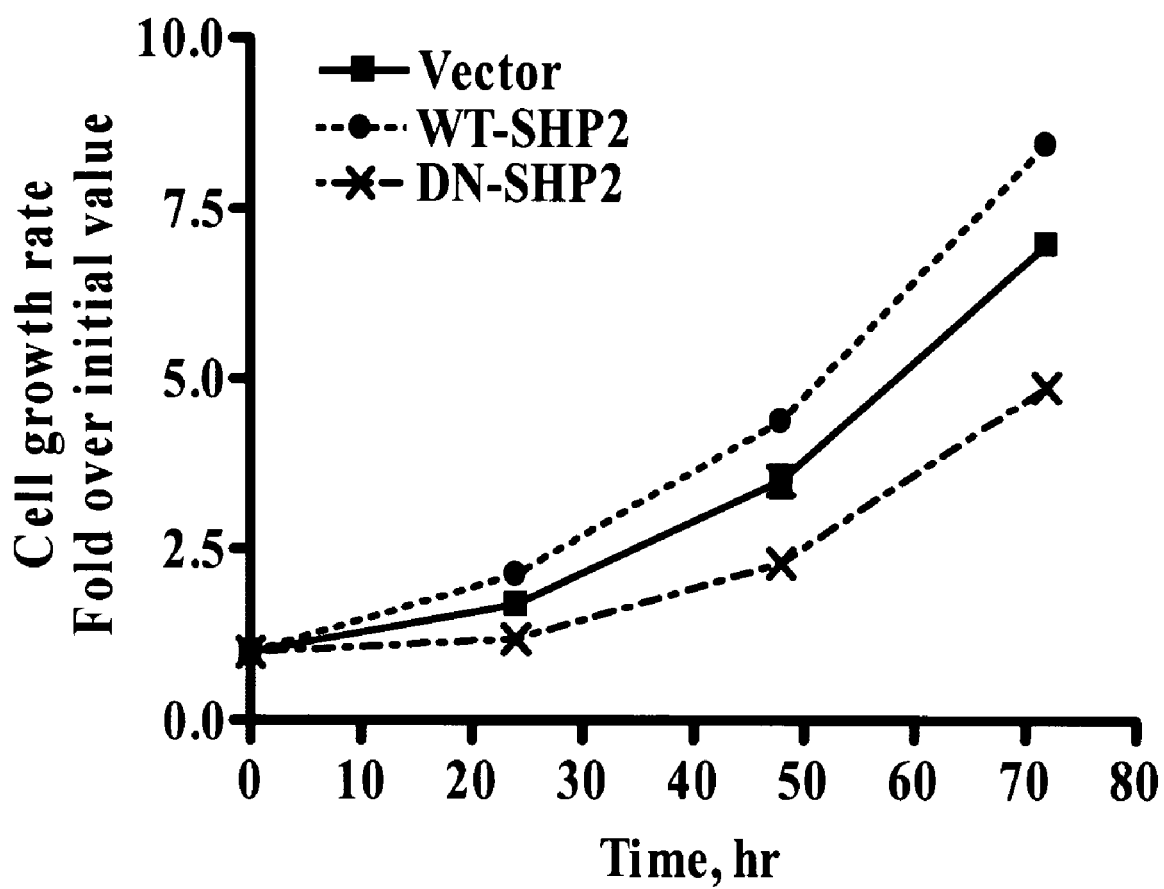
FIG. 2 is suppression of cell proliferation by the expression of DN-SHP2 in the BT474 breast cancer cell line.
Figure 3:
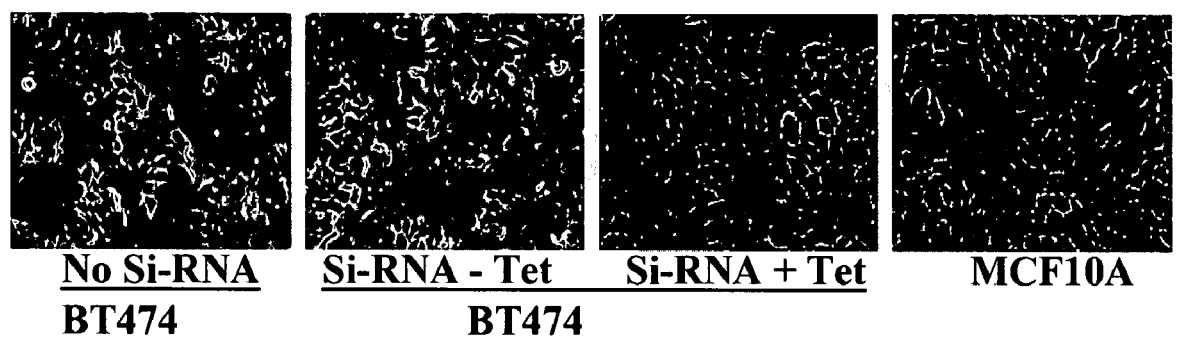
FIG. 3 is induction of a normal epithelial phenotype in the BT474 breast cancer cells by Si-RNA-mediated ablation of the SHP2 protein
Figure 4:
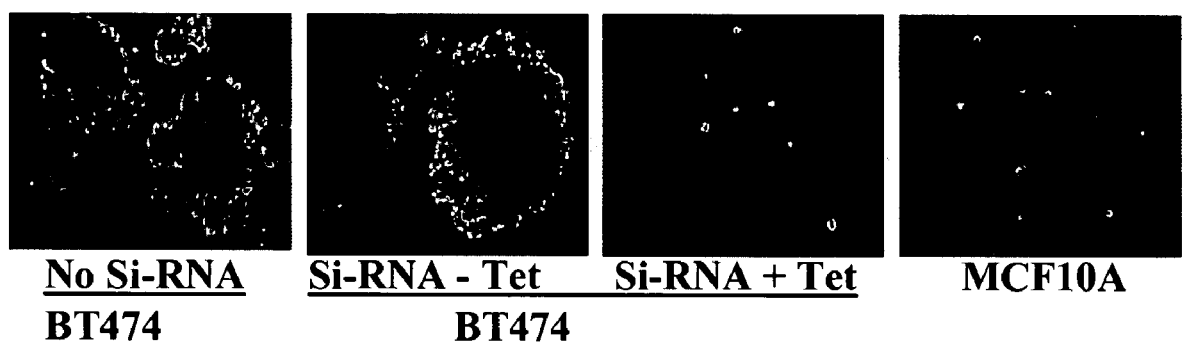
FIG. 4 is inhibition of anchorage-independent growth ability of the BT474 breast cancer cells in soft agar by Si-RNA-mediated ablation of the SHP2 protein.
Figure 5:
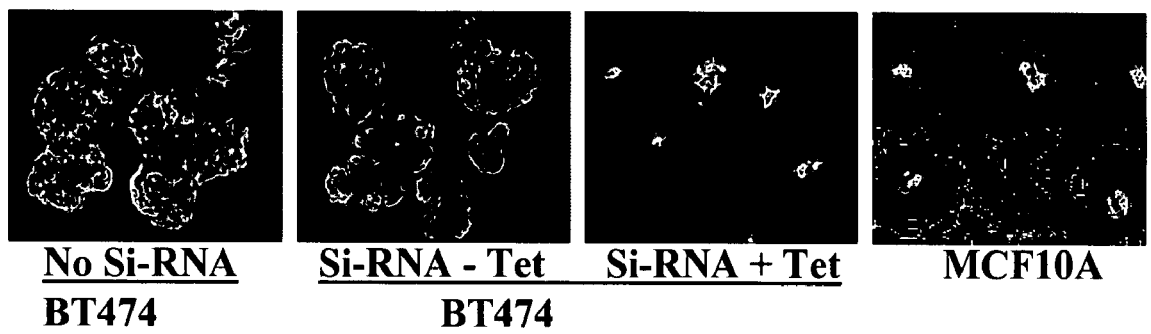
FIG. 5 is induction of re-differentiation in the BT474 breast cancer cells to a normal acin-forming breast epithelial cells.
Figure 6:
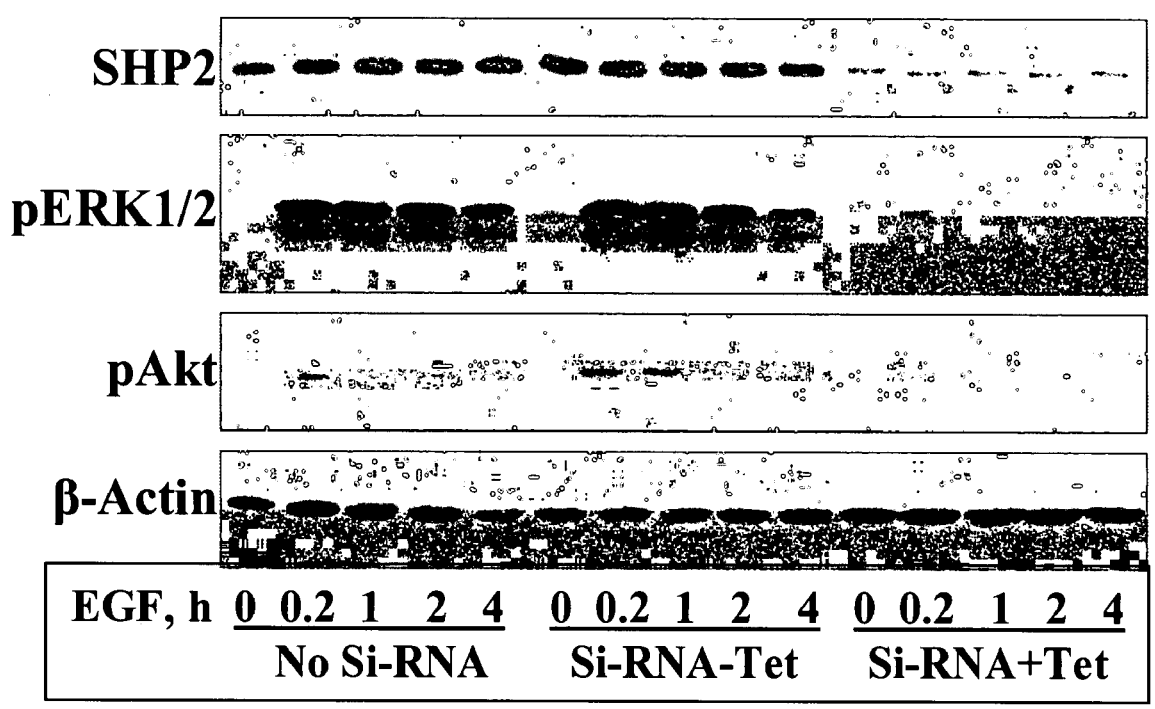
FIG. 6 is inhibition of epidermal growth factor-induced activation of ERK1/2 and Akt in the BT474 breast cancer cells by Si-RNA-mediated ablation of the SHP2 protein.
Figure 7:
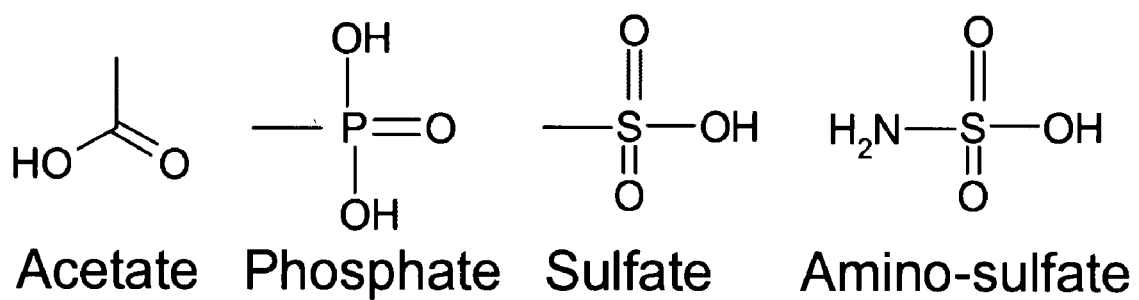
FIG. 7 are the functional groups for the modification of the WGMDY peptides at the Tyr residue or the R' modification of the SEBA derivatives.

As outlined above, biological substrates of SHP2 were isolated by substrate-trapping techniques and then identified by a combination of mass spectroscopic and immunoblotting analysis (4, 5, 23). By employing site-directed mutagenesis, binding studies and functional analysis of mutants, target Tyr residues for the SHP2 phosphatase activity were identified (23, 61). Further site-directed mutagenesis and binding studies and computer-based comparison (FASTA) of amino acid sequences surrounding target Tyr residues showed a potential consensus motif for recognition of substrates by the active site of the SHP2 phosphatase domain. The characteristic features of this consensus motif are the Y (Tyr) residue that acts as a substrate when phosphorylated, the invariable D (Asp) residue at the −2 position (the amino acid immediately N-terminal to the Y is referred to as −1), hydrophobic residues at the −1 and −3 positions and a D or E (Glu) residue at the −4 position (FIG. 7). As is known in the art, amino acids in WGMDY peptides are covalently linked to each other through what is known as peptide bond. As is also known in the art, peptide bonds are formed between the carboxyl group of the N-terminal amino acid and the amine group of the next amino acid and so on.

Accumulating evidence indicates that SHP2 could serve as a therapeutic target for the treatment of cancer. In the context of the current invention, this conclusion is based on the following findings. First, SHP2 is a positive effector of EGFR and HER2 signaling and cell transformation receptors. And secondly, SHP2 is required for EGFR- and HER2-induced activation of β-catenin, the major transducer of the Wnt signaling pathway. Thus, SHP2 integrates the EGFR/HER2 and β-catenin signaling pathways. Because aberrant signaling by the EGFR, HER2 and β-catenin is implicated in the development of a variety of cancers, inhibition of SHP2 has the potential for cancer treatment Aberrant EGFR and HER2 signaling is strongly associated with aggressive tumor growth which correlates with poor prognosis for patient survival. As a result, there has been a great deal of interest in the production of drugs that inactivate EGFR and HER2 in tumors. Approximately 50% of breast, ovarian, colorectal and lung cancers overexpress EGFR or HER2 due to gene amplification, and of these, the majority have gene rearrangements that result in constitutive activation of these receptors (44, 64, 67, 77, 101). Currently, several drugs that interfere with the functions of these proteins have been produced. Some are already in clinical use while others are in advanced stage of clinical trials. However, there have not been any breakthroughs. For instance, herceptin, the anti-HER2 drug currently in clinical use for breast cancer, slows tumor progression in only 30% of the patients. In the pipeline are drugs that interfere with the Tyr kinase domains of EGFR and HER2, most notably, traceva (erlotinib) and iressa (gefitinib). Traceva and iressa are currently in advanced clinical trials. Unfortunately, the outcome of these trials has not been promising. For instance, patients treated with standard chemotherapy in combination with Iressa did not show any significant increase in overall survival rates than those treated with chemotherapy alone (31, 68, 75). Although these drugs provide some benefit by lengthening the life of the patient by several months to few a years, the cancer usually recurs and the patient eventually dies even after combination therapy with other non-specific agents such as paclitaxel and cisplatin. The common problem in the treatment of breast and other forms of cancer has been the ability of a cancer cell to adjust and overcome targeted chemotherapy by activating parallel growth signals. Because SHP2 is an essential downstream effector of EGFR and HER2, inhibition of SHP2 with drugs that will be developed from pWGMDY and SEBA derivatives will have a much better outcome than anti-EGFR and anti-HER2 drugs.

Increased Wnt signaling either due to the presence of an abnormally high amount of Wnt ligands or defects in one or more of the multiprotein complexes that channel cytoplasmic β-catenin for degradation, results in stabilization of β-catenin leading to its translocation to the nucleus where it induces the expression of mitogenic genes (11, 16, 18, 20, 37, 60). In support of this phenomenon, MMTV-LTR-driven overexpressing of Wnt1 or constitutively active β-catenin or knockout of α-catenin expression consistently resulted in a hyperplastic breast tissue (40, 91). Therefore, biochemical defects that ultimately result in deregulated β-catenin can induce epithelial to mesenchymal transition ("EMT") leading to cell transformation and tumor growth in the breast or other tissues. The similarity of α-catenin knockout to constitutively active β-catenin indicate that interference with α-catenin could also result in β-catenin stabilization and translocation to the nucleus. The findings in fibroblasts transformed with the constitutively active FGFR3 (23) and in the BT474 breast cancer cell line showed that SHP2 interferes with Tyr phosphorylation-dependent interaction of α-catenin with β-catenin. Therefore, under conditions of elevated Tyr phosphorylation, such as overexpression of EGFR or HER2, SHP2 can activate β-catenin even without Wnt stimulation.

Figure 11:
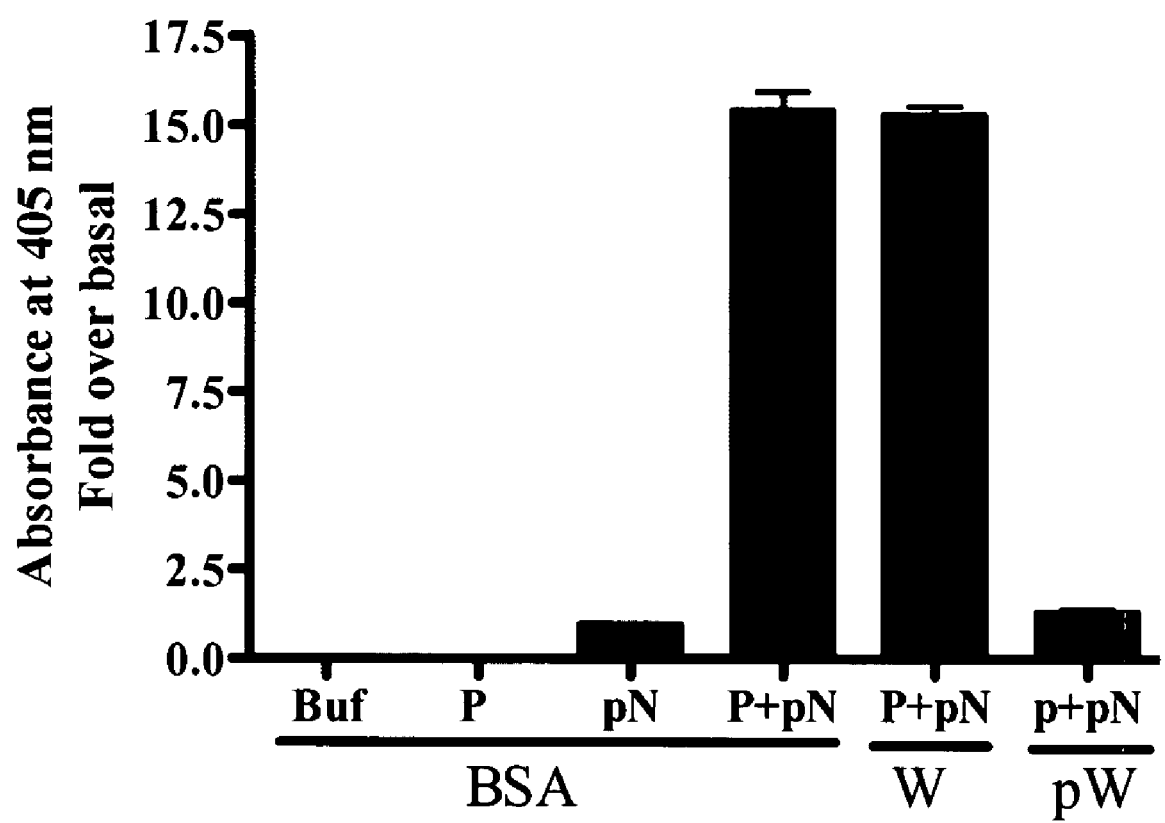
FIG. 11 is the anti-SHP2 peptide pWGMDY1 inhibition of phosphatase activity of SHP2.
Figure 12:
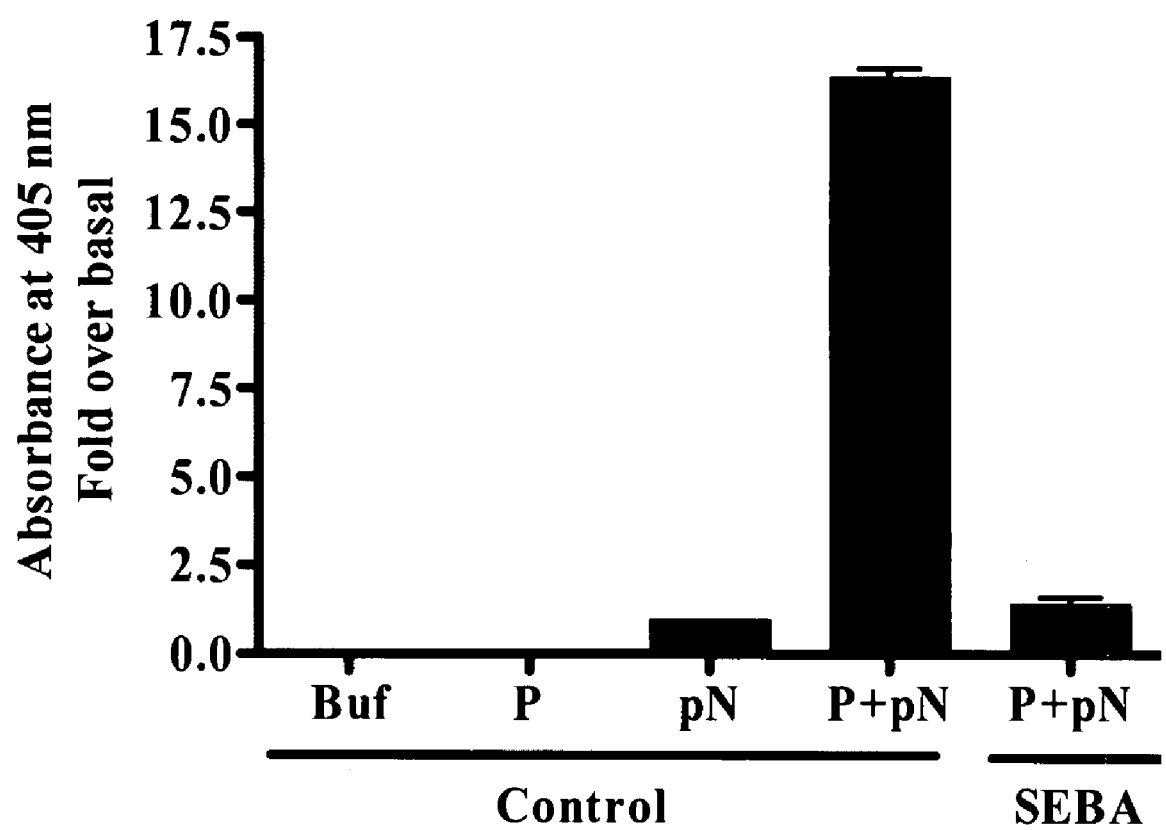
FIG. 12 is the SEBA inhibition of phophastase activity of SHP2 shown in a protein gel.

To provide evidence on the use of WGMDY peptides to inhibit SHP2 function, WGMDY1 was fused to a 10-mer cell-penetrating peptide sequence of HIV tat-1 protein (85, 90, 94, 98) to aid internalization and custom synthesized as a phosphorylated form (pWGMDY1) and unphosphorylated form (WGMDY1). The anti-SHP2 effect of these preparations were first tested by in vitro phosphatase assays using purified glutathione S-transferase (GST) fusion of the phosphatase domain of SHP2 (denoted as P) as an enzyme and para-nitrophenolphosphate (denoted as pN) as an artificial substrate as described recently (61). Reactions containing buffer, P and pN only were used as negative controls for the dephosphorylation reactions. Para-nitrophenol phosphate (pN) is colorless in solution and as such has very low optical density. But, when dephosphorylated to para-nitrophenol, it exhibits a yellowish discoloration, acquiring an increased optical density that can be measured with a spectrophotometer. Absorption of visible light by para-nitrophenol phosphate peaks at a wave length of 405 nm. Therefore, reactions were followed with absorbance measurement (OD) at 405 nm in a plate reader spectrophotometer (TECAN). Absorbance at the 5 minutes time point was used for comparing the effect of pWGMDY1 on the phosphatase activity of P. As described previously, dephosphorylation of pN by P was more than 15-fold over basal after a 5 minute incubation period (61). Addition of pWGMDY1, but not WGMDY1, inhibited the dephosphorylation reaction (FIG. 11). Similar results were obtained when SEBA was used in place of pWGMDY (FIG. 12). These results demonstrate that pWGMDY1 and SEBA are SHP2 inhibitors.

Figure 13:
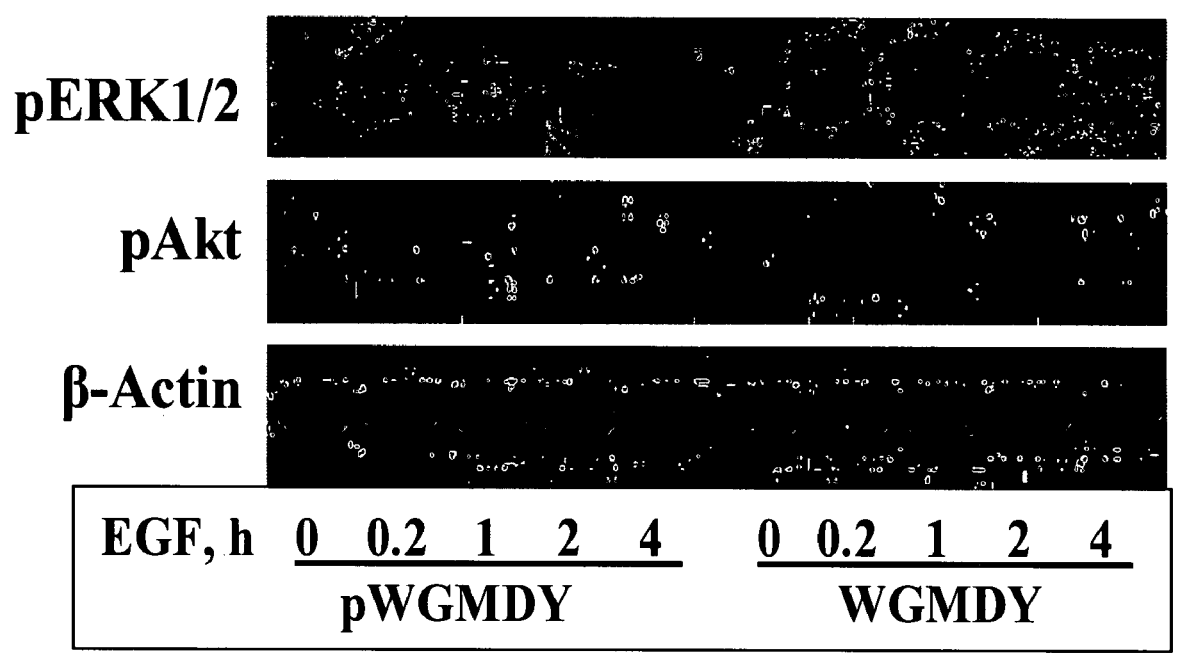
FIG. 13 is the effect of pWGMDY on EGF-induced ERK1/2 and AKT activation.

To determine that pWGMDY1 can also be used to inhibit SHP2 in cells, the following experiments were performed. The BT474 breast cancer cells were treated with 5 μg/ml of pWGMDY1 or WGMDY1 for 30 minutes. They were then stimulated with EGF for varying time points. Total cell lysates prepared from these cells were analyzed by immunoblotting with specific antibodies that recognize the activated forms of these proteins. As shown in FIG. 13, pWGMDY inhibited ERK1/2 and Akt activation, while WGMDY did not. Note that ERK1/2 and Akt activation was sustained for more than 2 hours in the control WGMDY1-treated cells, while it was submaximal even at the 10 minute time point in the pWGMDY1-treated cells. Anti-β-actin reblotting showed that total protein levels were comparable. These results demonstrate that pWGMDY1 inhibits the signal transduction role of SHP2 in intact cells.

REFERENCES CITED

1. Abutaily, A. S., J. E. Collins, and W. R. Roche. 2003. Cadherins, catenins and APC in pleural malignant mesothelioma. J Pathol 201:355-62.
2. Adachi, M., E. H. Fischer, J. Ihle, K. Imai, F. Jirik, B. Neel, T. Pawson, S. Shen, M. Thomas, A. Ullrich, and Z. Zhao. 1996. Mammalian SH2-containing protein tyrosine phosphatases. Cell 85:15.
3. Agazie, Y., I. Ischenko, and M. Hayman. 2002. Concomitant activation of the PI3K-Akt and the Ras-ERK signaling pathways is essential for transformation by the V-SEA tyrosine kinase oncogene. Oncogene 21:697-707.
4. Agazie, Y. M., and M. J. Hayman. 2003. Development of an efficient "substrate-trapping" mutant of Src homology phosphotyrosine phosphatase 2 and identification of the epidermal growth factor receptor, Gab1, and three other proteins as target substrates. J Biol Chem 278:13952-8.
5. Agazie, Y. M., and M. J. Hayman. 2003. Molecular mechanism for a role of SHP2 in epidermal growth factor receptor signaling. Mol Cell Biol 23:7875-86.
6. Agazie, Y. M., N. Movilla, I. Ischenko, and M. J. Hayman. 2003. The phosphotyrosine phosphatase SHP2 is a critical mediator of transformation induced by the oncogenic fibroblast growth factor receptor 3. Oncogene 22:6909-18.
7. Alonso, A., J. Sasin, N. Bottini, I. Friedberg, A. Osterman, A. Godzik, T. Hunter, J. Dixon, and T. Mustelin. 2004. Protein tyrosine phosphatases in the human genome. Cell 117:699-711.
8. Anderson, J., H. D. Burns, P. Enriquez-Harris, A. O. Wilkie, and J. K. Heath. 1998. Apert syndrome mutations in fibroblast growth factor receptor 2 exhibit increased affinity for FGF ligand. Hum Mol Genet 7:1475-83.
9. Araki, T., M. G. Mohi, F. A. Ismat, R. T. Bronson, I. R. Williams, J. L. Kutok, W. Yang, L. I. Pao, D. G. Gilliland, J. A. Epstein, and B. G. Neel. 2004. Mouse model of Noonan syndrome reveals cell type- and gene dosage-dependent effects of Ptpn11 mutation. Nat Med 10:849-57.
10. Araki, T., H. Nawa, and B. G. Neel. 2003. Tyrosyl phosphorylation of Shp2 is required for normal ERK activation in response to some, but not all, growth factors. J Biol Chem 278:41677-84.
11. Aust, D. E., J. P. Terdiman, R. F. Willenbucher, C. G. Chang, A. Molinaro-Clark, G. B. Baretton, U. Loehrs, and F. M. Waldman. 2002. The APC/beta-catenin pathway in ulcerative colitis-related colorectal carcinomas: a mutational analysis. Cancer 94:1421-7.
12. Bardelli, A., P. Longati, D. Gramaglia, M. C. Stella, and P. M. Comoglio. 1997. Gab1 coupling to the HGF/Met receptor multifunctional docking site requires binding of Grb2 and correlates with the transforming potential. Oncogene 15:3103-11.
13. Barth, A. I., I. S. Nathke, and W. J. Nelson. 1997. Cadherins, catenins and APC protein: interplay between cytoskeletal complexes and signaling pathways. Curr Opin Cell Biol 9:683-90.
14. Bennett, A. M., S. F. Hausdorff, A. M. O'Reilly, R. M. Freeman, and B. G. Neel. 1996. Multiple requirements for SHPTP2 in epidermal growth factor-mediated cell cycle progression. Mol Cell Biol 16:1189-202.
15. Bentires-Alj, M., J. G. Paez, F. S. David, H. Keilhack, B. Halmos, K. Naoki, J. M. Maris, A. Richardson, A. Bardelli, D. J. Sugarbaker, W. G. Richards, J. Du, L. Girard, J. D. Minna, M. L. Loh, D. E. Fisher, V. E. Velculescu, B. Vogelstein, M. Meyerson, W. R. Sellers, and B. G. Neel. 2004. Activating mutations of the noonan syndrome-associated SHP2/PTPN11 gene in human solid tumors and adult acute myelogenous leukemia. Cancer Res 64:8816-20.
16. Bhatia, N., and V. S. Spiegelman. 2005. Activation of Wnt/beta-catenin/Tcf signaling in mouse skin carcinogenesis. Mol Carcinog 42:213-21.
17. Boggon, T. J., and M. J. Eck. 2004. Structure and regulation of Src family kinases. Oncogene 23:7918-27.
18. Brennan, K. R., and A. M. Brown. 2004. Wnt proteins in mammary development and cancer. J Mammary Gland Biol Neoplasia 9:119-31.
19. Brickell, P. M. 1992. The p60c-src family of protein-tyrosine kinases: structure, regulation, and function. Crit Rev Oncog 3:401-46.
20. Bright-Thomas, R. M., and R. Hargest. 2003. APC, beta-Catenin and hTCF-4; an unholy trinity in the genesis of colorectal cancer. Eur J Surg Oncol 29:107-17.
21. Brown, M. C., J. A. Perrotta, and C. E. Turner. 1996. Identification of LIM3 as the principal determinant of paxillin focal adhesion localization and characterization of a novel motif on paxillin directing vinculin and focal adhesion kinase binding. J Cell Biol 135:1109-23.
22. Bullions, L. C., D. A. Notterman, L. S. Chung, and A. J. Levine. 1997. Expression of wild-type alpha-catenin protein in cells with a mutant alpha-catenin gene restores both growth regulation and tumor suppressor activities. Mol Cell Biol 17:4501-8.
23. Burks, J., Agazie, Y., 2006. Modulation of Alpha Catenin Tyr Phosphorylation by SHP2 Positively Effects Cell Transformation Induced by the Constitutively Active FGFR3. Oncogene In Press.
24. Carlberg, K., and L. R. Rohrschneider. 1997. Characterization of a novel tyrosine phosphorylated 100-kDa protein that binds to SHP-2 and phosphatidylinositol 3'-kinase in myeloid cells. J Biol Chem 272:15943-50.
25. Chang, Y., B. Ceacareanu, M. Dixit, N. Sreejayan, and A. Hassid. 2002. Nitric oxide-induced motility in aortic smooth muscle cells: role of protein tyrosine phosphatase SHP-2 and GTP-binding protein Rho. Circ Res 91:390-7.
26. Chardin, P., J. H. Camonis, N. W. Gale, L. van Aelst, J. Schlessinger, M. H. Wigler, and D. Bar-Sagi. 1993. Human Sos1: a guanine nucleotide exchange factor for Ras that binds to GRB2. Science 260:1338-43.
27. Cooley, M. A., J. M. Broome, C. Ohngemach, L. H. Romer, and M. D. Schaller. 2000. Paxillin binding is not the sole determinant of focal adhesion localization or dominant-negative activity of focal adhesion kinase/focal adhesion kinase-related nonkinase. Mol Biol Cell 11:3247-63.
28. Cunnick, J. M., J. F. Dorsey, T. Munoz-Antonia, L. Mei, and J. Wu. 2000. Requirement of SHP2 binding to Grb2-associated binder-1 for mitogen-activated protein kinase activation in response to lysophosphatidic acid and epidermal growth factor. J Biol Chem 275:13842-8.
29. Deb, T. B., L. Wong, D. S. Salomon, G. Zhou, J. E. Dixon, J. S. Gutkind, S. A. Thompson, and G. R. Johnson. 1998. A common requirement for the catalytic activity and both SH2 domains of SHP-2 in mitogen-activated protein (MAP) kinase activation by the ErbB family of receptors. A specific role for SHP-2 in map, but not c-Jun amino-terminal kinase activation. J Biol Chem 273:16643-6.
30. Dionne, C. A., M. Jaye, and J. Schlessinger. 1991. Structural diversity and binding of FGF receptors. Ann N Y Acad Sci 638:161-6.
31. Eckhardt, S. 2006. Molecular targeted therapy: a strategy of disillusions or optimism? J Lab Clin Med 147:108-13.
32. Feng, G. S., C. C. Hui, and T. Pawson. 1993. SH2-containing phosphotyrosine phosphatase as a target of protein-tyrosine kinases. Science 259:1607-11.
33. Feng, G. S., and T. Pawson. 1994. Phosphotyrosine phosphatases with SH2 domains: regulators of signal transduction. Trends Genet 10:54-8.
34. Flint, A. J., T. Tiganis, D. Barford, and N. K. Tonks. 1997. Development of "substrate-trapping" mutants to identify physiological substrates of protein tyrosine phosphatases. Proc Natl Acad Sci USA 94:1680-5.
35. Frearson, J. A., and D. R. Alexander. 1998. The phosphotyrosine phosphatase SHP-2 participates in a multimeric signaling complex and regulates T cell receptor (TCR) coupling to the Ras/mitogen-activated protein kinase (MAPK) pathway in Jurkat T cells. J Exp Med 187:1417-26.
36. Garrett, T. P., N. M. McKern, M. Lou, T. C. Elleman, T. E. Adams, G. O. Lovrecz, M. Kofler, R. N. Jorissen, E. C. Nice, A. W. Burgess, and C. W. Ward. 2003. The crystal structure of a truncated ErbB2 ectodomain reveals an active conformation, poised to interact with other ErbB receptors. Mol Cell 11:495-505.
37. Gerstein, A. V., T. A. Almeida, G. Zhao, E. Chess, M. Shih Ie, K. Buhler, K. Pienta, M. A. Rubin, R. Vessella, and N. Papadopoulos. 2002. APC/CTNNB1 (beta-catenin) pathway alterations in human prostate cancers. Genes Chromosomes Cancer 34:9-16.
38. Hadari, Y. R., H. Kouhara, I. Lax, and J. Schlessinger. 1998. Binding of Shp2 tyrosine phosphatase to FRS2 is essential for fibroblast growth factor-induced PC12 cell differentiation. Mol Cell Biol 18:3966-73.
39. Hakak, Y., Y. S. Hsu, and G. S. Martin. 2000. Shp-2 mediates v-Src-induced morphological changes and activation of the anti-apoptotic protein kinase Akt. Oncogene 19:3164-71.
40. Hatsell, S., T. Rowlands, M. Hiremath, and P. Cowin. 2003. Beta-catenin and Tcfs in mammary development and cancer. J Mammary Gland Biol Neoplasia 8:145-58.
41. Hof, P., S. Pluskey, S. Dhe-Paganon, M. J. Eck, and S. E. Shoelson. 1998. Crystal structure of the tyrosine phosphatase SHP-2. Cell 92:441-50.
42. Holbro, T., R. R. Beerli, F. Maurer, M. Koziczak, C. F. Barbas, 3rd, and N. E. Hynes. 2003. The ErbB2/ErbB3 heterodimer functions as an oncogenic unit: ErbB2 requires ErbB3 to drive breast tumor cell proliferation. Proc Natl Acad Sci USA 100:8933-8.
43. Honegger, A. M., A. Schmidt, A. Ullrich, and J. Schlessinger. 1990. Evidence for epidermal growth factor (EGF)-induced intermolecular autophosphorylation of the EGF receptors in living cells. Mol Cell Biol 10:4035-44.
44. Huang, H. S., M. Nagane, C. K. Klingbeil, H. Lin, R. Nishikawa, X. D. Ji, C. M. Huang, G. N. Gill, H. S. Wiley, and W. K. Cavenee. 1997. The enhanced tumorigenic activity of a mutant epidermal growth factor receptor common in human cancers is mediated by threshold levels of constitutive tyrosine phosphorylation and unattenuated signaling. J Biol Chem 272:2927-35.
45. Hubbard, S. R., and J. H. Till. 2000. Protein tyrosine kinase structure and function. Annu Rev Biochem 69:373-98.
46. Inagaki, K., T. Noguchi, T. Matozaki, T. Horikawa, K. Fukunaga, M. Tsuda, M. Ichihashi, and M. Kasuga. 2000. Roles for the protein tyrosine phosphatase SHP-2 in cytoskeletal organization, cell adhesion and cell migration revealed by overexpression of a dominant negative mutant. Oncogene 19:75-84.
47. Ingley, E., and S. P. Klinken. 2006. Cross-regulation of JAK and Src kinases. Growth Factors 24:89-95.
48. Johnson, D. E., and L. T. Williams. 1993. Structural and functional diversity in the FGF receptor multigene family. Adv Cancer Res 60:1-41.
49. Kobielak, A., and E. Fuchs. 2004. Alpha-catenin: at the junction of intercellular adhesion and actin dynamics. Nat Rev Mol Cell Biol 5:614-25.
50. Kodama, A., T. Matozaki, A. Fukuhara, M. Kikyo, M. Ichihashi, and Y. Takai. 2000. Involvement of an SHP-2-Rho small G protein pathway in hepatocyte growth factor/scatter factor-induced cell scattering. Mol Biol Cell 11:2565-75.
51. Kuhne, M. R., T. Pawson, G. E. Lienhard, and G. S. Feng. 1993. The insulin receptor substrate 1 associates with the SH2-containing phosphotyrosine phosphatase Syp. J Biol Chem 268:11479-81.
52. Lacalle, R. A., E. Mira, C. Gomez-Mouton, S. Jimenez-Baranda, A. C. Martinez, and S. Manes. 2002. Specific SHP-2 partitioning in raft domains triggers integrin-mediated signaling via Rho activation. J Cell Biol 157:277-89.
53. Lechleider, R. J., R. M. Freeman, Jr., and B. G. Neel. 1993. Tyrosyl phosphorylation and growth factor receptor association of the human corkscrew homologue, SH-PTP2. J Biol Chem 268:13434-8.
54. Lechleider, R. J., S. Sugimoto, A. M. Bennett, A. S. Kashishian, J. A. Cooper, S. E. Shoelson, C. T. Walsh, and B. G. Neel. 1993. Activation of the SH2-containing phosphotyrosine phosphatase SH-PTP2 by its binding site, phosphotyrosine 1009, on the human platelet-derived growth factor receptor. J Biol Chem 268:21478-81.
55. Lechleider, R. J., S. Sugimoto, A. M. Bennett, A. S. Kashishian, J. A. Cooper, S. E. Shoelson, C. T. Walsh, and B. G. Neel. 1993. Activation of the SH2-containing phosphotyrosine phosphatase SR-PTP2 by its binding site, phosphotyrosine 1009, on the human platelet-derived growth factor receptor. J Biol Chem 268:21478-81.
56. Manes, S., E. Mira, C. Gomez-Mouton, Z. J. Zhao, R. A. Lacalle, and A. C. Martinez. 1999. Concerted activity of tyrosine phosphatase SHP-2 and focal adhesion kinase in regulation of cell motility. Mol Cell Biol 19:3125-35.
57. Margolis, B., N. Li, A. Koch, M. Mohammadi, D. R. Hurwitz, A. Zilberstein, A. Ulirich, T. Pawson, and J. Schlessinger. 1990. The tyrosine phosphorylated carboxy-terminus of the EGF receptor is a binding site for GAP and PLC-gamma. Embo J 9:4375-80.
58. Massoglia, S., A. Gray, T. J. Dull, S. Munemitsu, H. J. Kun, J. Schiessinger, and A. Ullrich. 1990. Epidermal growth factor receptor cytoplasmic domain mutations trigger ligand-independent transformation. Mol Cell Biol 10:3048-55.
59. Melillo, R. M., M. Santoro, S. H. Ong, M. Billaud, A. Fusco, Y. R. Hadari, J. Schlessinger, and I. Lax. 2001. Docking protein FRS2 links the protein tyrosine kinase RET and its oncogenic forms with the mitogen-activated protein kinase signaling cascade. Mol Cell Biol 21:4177-87.
60. Meniel, V., and A. R. Clarke. 2003. Wnt-cadherin connections in normal and neoplastic mammary epithelium. J Mammary Gland Biol Neoplasia 8:435-47.

61. Merritt, R., M. J. Hayman, and Y. M. Agazie. 2006. Mutation of Thr466 in SHP2 abolishes its phosphatase activity, but provides a new substrate-trapping mutant. Biochim Biophys Acta 1763:45-56.
62. Mohi, M. G., I. R. Williams, C. R. Dearolf, G. Chan, J. L. Kutok, S. Cohen, K. Morgan, C. Boulton, H. Shigematsu, H. Keilhack, K Akashi, D. G. Gilliland, and B. G. Neel. 2005. Prognostic, therapeutic, and mechanistic implications of a mouse model of leukemia evoked by Shp2 (PTPN11) mutations. Cancer Cell 7:179-91.
63. Morton, R. A., C. M. Ewing, A. Nagafuchi, S. Tsukita, and W. B. Isaacs. 1993. Reduction of E-cadherin levels and deletion of the alpha-catenin gene in human prostate cancer cells. Cancer Res 53:3585-90.
64. Nagane, M., F. Coufal, H. Lin, O. Bogler, W. K. Cavenee, and H. J. Huang. 1996. A common mutant epidermal growth factor receptor confers enhanced tumorigenicity on human glioblastoma cells by increasing proliferation and reducing apoptosis. Cancer Res 56:5079-86.
65. Nakamoto, T., R. Sakai, K. Ozawa, Y. Yazaki, and H. Hirai. 1996. Direct binding of C-terminal region of p130Cas to SH2 and SH3 domains of Src kinase. J Biol Chem 271:8959-65.
66. Neel, B. G., and N. K. Tonks. 1997. Protein tyrosine phosphatases in signal transduction. Curr Opin Cell Biol 9:193-204.
67. Nishikawa, R., X. D. Ji, R. C. Harmon, C. S. Lazar, G. N. Gill, W. K. Cavenee, and H. J. Huang. 1994. A mutant epidermal growth factor receptor common in human glioma confers enhanced tumorigenicity. Proc Natl Acad Sci USA 91:7727-31.
68. Normanno, N., A. D. Luca, M. R. Maiello, M. Campiglio, M. Napolitano, M. Mancino, A. Carotenuto, G. Viglietto, and S. Menard. 2006. The MEK/MAPK pathway is involved in the resistance of breast cancer cells to the EGFR tyrosine kinase inhibitor gefitinib. J Cell Physiol 207:420-7.
69. O'Reilly, A. M., and B. G. Neel. 1998. Structural determinants of SHP-2 function and specificity in Xenopus mesoderm induction. Mol Cell Biol 18:161-77.
70. O'Reilly, A. M., S. Pluskey, S. E. Shoelson, and B. G. Neel. 2000. Activated mutants of SHP-2 preferentially induce elongation of Xenopus animal caps. Mol Cell Biol 20:299-311.
71. Ong, S. H., G. R. Guy, Y. R. Hadari, S. Laks, N. Gotoh, J. Schlessinger, and I. Lax. 2000. FRS2 proteins recruit intracellular signaling pathways by binding to diverse targets on fibroblast growth factor and nerve growth factor receptors. Mol Cell Biol 20:979-89.
72. Parsons, J. T. 2003. Focal adhesion kinase: the first ten years. J Cell Sci 116:1409-16.
73. Parsons, S. J., and J. T. Parsons. 2004. Src family kinases, key regulators of signal transduction. Oncogene 23:7906-9.
74. Pawson, T., and G. D. Gish. 1992. SH2 and SH3 domains: from structure to function. Cell 71:359-62.
75. Perez-Soler, R. 2004. HER1/EGFR targeting: refining the strategy. Oncologist 9:58-67.
76. Polte, T. R., and S. K. Hanks. 1997. Complexes of focal adhesion kinase (FAK) and Crk-associated substrate (p130 (Cas)) are elevated in cytoskeleton-associated fractions following adhesion and Src transformation. Requirements for Src kinase activity and FAK proline-rich motifs. J Biol Chem 272:5501-9.
77. Ro, J., S. M. North, G. E. Gallick, G. N. Hortobagyi, J. U. Gutterman, and M. Blick. 1988. Amplified and overexpressed epidermal growth factor receptor gene in uncultured primary human breast carcinoma. Cancer Res 48:161-4.
78. Saxton, T. M., B. G. Ciruna, D. Holmyard, S. Kulkarni, K. Harpal, J. Rossant, and T. Pawson. 2000. The SH2 tyrosine phosphatase shp2 is required for mammalian limb development. Nat Genet 24:420-3.
79. Saxton, T. M., M. Henkemeyer, S. Gasca, R. Shen, D. J. Rossi, F. Shalaby, G. S. Feng, and T. Pawson. 1997. Abnormal mesoderm patterning in mouse embryos mutant for the SH2 tyrosine phosphatase Shp-2. Embo J 16:2352-64.
80. Schaeper, U., N. H. Gehring, K. P. Fuchs, M. Sachs, B. Kempkes, and W. Birchmeier. 2000. Coupling of Gab1 to c-Met, Grb2, and Shp2 mediates biological responses. J Cell Biol 149:1419-32.
81. Schaller, M. D. 2001. Biochemical signals and biological responses elicited by the focal adhesion kinase. Biochim Biophys Acta 1540:1-21.
82. Schlessinger, J. 2000. Cell signaling by receptor tyrosine kinases. Cell 103:211-25.
83. Schlessinger, J., M. Mohammadi, B. Margolis, and A. Ullrich. 1992. Role of SH2-containing proteins in cellular signaling by receptor tyrosine kinases. Cold Spring Harb Symp Quant Biol 57:67-74.
84. Schoenwaelder, S. M., L. A. Petch, D. Williamson, R. Shen, G. S. Feng, and K. Burridge. 2000. The protein tyrosine phosphatase Shp-2 regulates RhoA activity. Curr Biol 10:1523-6.
85. Snyder, E. L., and S. F. Dowdy. 2004. Cell penetrating peptides in drug delivery. Pharm Res 21:389-93.
86. Tang, T. L., R. M. Freeman, Jr., A. M. O'Reilly, B. G. Neel, and S. Y. Sokol. 1995. The SH2-containing protein-tyrosine phosphatase SH-PTP2 is required upstream of MAP kinase for early Xenopus development. Cell 80:473-83.
87. Tartaglia, M., S. Martinelli, I. Iavarone, G. Cazzaniga, M. Spinelli, E. Giarin, V. Petrangeli, C. Carta, R. Masetti, M. Arico, F. Locatelli, G. Basso, M. Sorcini, A. Pession, and A. Biondi. 2005. Somatic PTPN11 mutations in childhood acute myeloid leukaemia. Br J Haematol 129:333-9.
88. Tartaglia, M., E. L. Mehler, R. Goldberg, G. Zampino, H. G. Brunner, H. Kremer, I. van der Burgt, A. H. Crosby, A. Ion, S. Jeffery, K. Kalidas, M. A. Patton, R. S. Kucherlapati, and B. D. Gelb. 2001. Mutations in PTPN11, encoding the protein tyrosine phosphatase SHP-2, cause Noonan syndrome. Nat Genet 29:465-8.
89. Tartaglia, M., C. M. Niemeyer, A. Fragale, X. Song, J. Buechner, A. Jung, K. Hahlen, H. Hasle, J. D. Licht, and B. D. Gelb. 2003. Somatic mutations in PTPN11 in juvenile myelomonocytic leukemia, myelodysplastic syndromes and acute myeloid leukemia. Nat Genet 34:148-50.
90. Temsamani, J., and P. Vidal. 2004. The use of cell-penetrating peptides for drug delivery. Drug Discov Today 9:1012-9.
91. Teuliere, J., M. M. Faraldo, M. A. Deugnier, M. Shtutman, A. Ben-Ze'ev, J. P. Thiery, and M. A. Glukhova. 2005. Targeted activation of beta-catenin signaling in basal mammary epithelial cells affects mammary development and leads to hyperplasia. Development 132:267-77.
92. Tomic, S., U. Greiser, R. Lammers, A. Kharitonenkov, E. Imyanitov, A. Ullrich, and F. D. Bohmer. 1995. Association of SH2 domain protein tyrosine phosphatases with the epidermal growth factor receptor in human tumor cells. Phosphatidic acid activates receptor dephosphorylation by PTP1C. J Biol Chem 270:21277-84.

93. Tonks, N. K., and B. G. Neel. 1996. From form to function: signaling by protein tyrosine phosphatases. Cell 87:365-8.
94. Trehin, R., and H. P. Merkle. 2004. Chances and pitfalls of cell penetrating peptides for cellular drug delivery. Eur J Pharm Biopharm 58:209-23.
95. Ullrich, A., L. Coussens, J. S. Hayflick, T. J. Dull, A. Gray, A. W. Tam, J. Lee, Y. Yarden, T. A. Libermann, J. Schiessinger, and et al. 1984. Human epidermal growth factor receptor cDNA sequence and aberrant expression of the amplified gene in A431 epidermoid carcinoma cells. Nature 309:418-25.
96. Ullrich, A., and J. Schlessinger. 1990. Signal transduction by receptors with tyrosine kinase activity. Cell 61:203-12.
97. Vasioukhin, V., C. Bauer, L. Degenstein, B. Wise, and E. Fuchs. 2001. Hyperproliferation and defects in epithelial polarity upon conditional ablation of alpha-catenin in skin. Cell 104:605-17.
98. Vives, E., P. Brodin, and B. Lebleu. 1997. A truncated HIV-1 Tat protein basic domain rapidly translocates through the plasma membrane and accumulates in the cell nucleus. J Biol Chem 272:16010-7.
99. Wade, R., J. Bohl, and S. Vande Pol. 2002. Paxillin null embryonic stem cells are impaired in cell spreading and tyrosine phosphorylation of focal adhesion kinase. Oncogene 21:96-107.
100. Xu, H., K. W. Lee, and M. Goldfarb. 1998. Novel recognition motif on fibroblast growth factor receptor mediates direct association and activation of SNT adapter proteins. J Biol Chem 273:17987-90.
101. Xu, Y. H., N. Richert, S. Ito, G. T. Merlino, and I. Pastan. 1984. Characterization of epidermal growth factor receptor gene expression in malignant and normal human cell lines. Proc Natl Acad Sci USA 81:7308-12.
102. Yu, D. H., C. K. Qu, O. Henegariu, X. Lu, and G. S. Feng. 1998. Protein-tyrosine phosphatase Shp-2 regulates cell spreading, migration, and focal adhesion. J Biol Chem 273:21125-31.

What is claimed is:

1. An anti-SHP2 peptide consisting of a purified amino acid sequence selected from the group consisting of SEQ ID NO: 1; SEQ ID NO: 2; SEQ ID NO: 3; SEQ ID NO: 4; and SEQ ID NO: 5 or a conservative variant thereof wherein said conservative variant is Glu for Asp at −4, Asp for Glu at −4, Val for Gly at −2 and Gly for Val at −2 wherein said peptide is able to inhibit SHP2 without binding the SH2 domain.

2. The anti-SHP2 peptide of claim 1 further comprising the addition of a functional group selected from the group consisting of acetate, phosphate, sulfate, and aminosulfate wherein said functional group is covalently linked to the hydroxyl group of a tyrosine on said peptide wherein said functional group is acetate.

3. An isolated peptide consisting of a Tyr residue as a substrate, a Asp residue at the −2 position, hydrophobic residues at the −1 and −3 positions and either an Asp or a Glu residue at the −4 position wherein the peptide is able to block the phosphatase domain of SHP2 without binding SH2 and wherein the peptide consists of 5 residues.

4. The isolated peptide able to block the phosphatase domain of SHP2 of claim 3 further comprising the addition of a functional group selected from the group consisting of acetate, phosphate, sulfate, and aminosulfate wherein said functional group is covalently linked to the hydroxyl group of a tyrosine on said peptide.

5. The anti-SHP2 peptide of claim 1 further comprising the addition of a functional group selected from the group consisting of acetate, phosphate, sulfate, and aminosulfate wherein said functional group is covalently linked to the hydroxyl group of a tyrosine on said peptide wherein said functional group is phosphate.

6. The anti-SHP2 peptide of claim 1 further comprising the addition of a functional group selected from the group consisting of acetate, phosphate, sulfate, and aminosulfate wherein said functional group is covalently linked to the hydroxyl group of a tyrosine on said peptide wherein said functional group is sulfate.

7. The anti-SHP2 peptide of claim 1 further comprising the addition of a functional group selected from the group consisting of acetate, phosphate, sulfate, and aminosulfate wherein said functional group is covalently linked to the hydroxyl group of a tyrosine on said peptide wherein said functional group is amino sulfate.

* * * * *

UNITED STATES PATENT AND TRADEMARK OFFICE
CERTIFICATE OF CORRECTION

| | | |
|---|---|---|
| PATENT NO. | : 7,547,760 B2 | Page 1 of 1 |
| APPLICATION NO. | : 11/480814 | |
| DATED | : June 16, 2009 | |
| INVENTOR(S) | : Yehenew Mekonnen Agazie et al. | |

It is certified that error appears in the above-identified patent and that said Letters Patent is hereby corrected as shown below:

Col. 1, Line 5-10 should read
--This invention was funded at least in part by a grant from the United States government (awarded by NIH Grant No. R01 CA12940) and the United States Government has certain rights in the invention--

Signed and Sealed this

Twenty-first Day of July, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,547,760 B2  Page 1 of 1
APPLICATION NO. : 11/480814
DATED : June 16, 2009
INVENTOR(S) : Yehenew Mekonnen Agazie It is certified that error appears in the above-identified patent and that said Letters Patent is hereby corrected as shown below:

Title Page, Item [75] Inventor: Peter M. Mannett should be:

Peter M. Gannett

Signed and Sealed this

Twenty-third Day of November, 2010

David J. Kappos
*Director of the United States Patent and Trademark Office*